United States Patent [19]
McCallister

[11] Patent Number: 5,360,011
[45] Date of Patent: Nov. 1, 1994

[54] BLOOD SAMPLE COLLECTION

[76] Inventor: Teresa D. McCallister, Rte. 1, 45 Pine Pl., Mount Hope, W. Va. 25880

[21] Appl. No.: 90,621

[22] Filed: Jul. 13, 1993

[51] Int. Cl.$^5$ ............................................. A61B 5/00
[52] U.S. Cl. ................................................ 128/763
[58] Field of Search ........................ 128/760, 763–766, 128/770

[56] References Cited

U.S. PATENT DOCUMENTS

| | | | |
|---|---|---|---|
| 3,706,305 | 12/1972 | Berger et al. | |
| 4,041,934 | 8/1977 | Genese | 128/763 |
| 4,392,499 | 7/1983 | Towse | 128/764 |
| 4,444,203 | 4/1984 | Engelman | 128/764 |
| 4,731,059 | 3/1988 | Wanderer et al. | 604/192 |
| 5,086,780 | 2/1992 | Schmitt | 128/763 |
| 5,133,362 | 7/1992 | Moss | 128/763 |

Primary Examiner—Max Hindenburg
Attorney, Agent, or Firm—James Creighton Wray

[57] ABSTRACT

A blood sample collection kit has a syringe body, an open lumen needle, an elongated vacuum plunger for use with the syringe, and a pulling flange, a rubber sleeve covered transfer needle and screw threads at a distal end of the plunger for receiving a blood tube holder and a vacuum-type blood sample collection tube. The kit provides easy blood collection and blood transfer. The plunger body has a rubberized seal end and a flange on the opposite end. A rubber sleeve covered transfer needle is integrally formed above the flange. Screw threads connected the plunger body and a blood tube holder, which receives a vacuum-type blood sample collection tube. The vacuum plunger is inserted into a syringe and a blood tube holder is screwed onto the screw threads. A vacuum-type blood sample collection tube is inserted into the blood tube holder. Blood is obtained by manual aspiration through the access needle placed on the syringe and travels through an end-to-end tubular channel along the body of the plunger, and then is transferred to a blood sample collection tube by pushing a stopper of a vacuum-type sample collection tube against the rubber covered transfer needle, retracting the rubber covering, pushing the transfer needle through the stopper and opening the path for blood to flow into the reduced pressure in the collection tube.

44 Claims, 1 Drawing Sheet

BLOOD SAMPLE COLLECTION

BACKGROUND OF THE INVENTION

The present invention relates to blood sample collection and is directed particularly to improve devices used to collect and manually transfer blood, making them more efficient and reducing risk of blood contamination. The invention relates to an integrated assembly and apparatus for the collection of samples of blood specimens.

Historically, blood samples were taken by aspirating blood into a syringe and by manually transferring blood from the syringe into test tubes.

Vacuum-type blood sample collection tubes are used with tubular holders which have an internal threaded boss at one end to receive a double-ended sterile needle. The double-ended needle assembly has an upper transfer needle and an lower access needle which are joined at a base with external threads. First and second hard plastic covers with telescoping open ends cover the needles. Breaking a central seal by twisting the caps and pulling off the first cap exposes the rubber sleeve covered transfer needle and threaded base. Holding the second cap, which is interference-fit with cruciform flanges on the base, enables the engaging and tightening of the threads. The needle end, which fits through the boss and extends into the holder lumen, is covered with a thin flexible rubber cover. The lower access needle is covered with the second hard plastic cap. A vacuum-type collection tube is pushed part way into the holder with the stopper spaced from the upper needle. The hard cap is removed and the lower needle pierces a vein. Then the collection tube is pushed over the upper needle, and blood flows into the tube. With the holder in place, that tube may be removed and others may be pushed on the upper needle to obtain multiple samples.

The use of the small holder, although not difficult for trained medical technicians, requires finger strength and dexterity. Holding the holder in place with the lower needle in a vein while pushing and pulling vacuum-type blood sample collecting tubes may be mastered by medical technicians.

All medical professionals have experience in using standard syringes. The dexterity in using the syringes is the result of many repeated uses, both for sampling fluids and for injecting drugs, either directly from or into veins or from or into catheters.

In blood collection and sample tube filling for analysis and medical diagnosis or research, it is necessary to manually transfer blood from syringes to blood collection tubes. That is usually done by manual aspiration of blood from a catheter central line or vein into a syringe with a conventional plunger, followed by manual transfer of blood into vacuum-type blood collection tubes. This manual transfer increases the risk of blood contamination and the time required for blood collection procedure, consequently affecting the accuracy of blood test results. It also increases the risk of infecting the clinician as he/she holds a blood collection tube in her/his hand and forces a contaminated needle through its top. There is a great risk for an accidental needle stick during this process and consequent contamination of the clinician.

Direct venipuncture does not require manual transfer of blood to a collection tube since flashback of blood occurs readily. Collection of blood from a central line access requires manual aspiration of blood into a syringe and subsequent manual transfer into a blood collection tube. The devices available in the market will not simultaneously transfer a blood sample from a central line access to a tube since flashback of blood does not occur.

Collection of blood by means of direct venipuncture is not feasible in certain patients. In general, those patients suffer from severe and/or prolonged illnesses, like Hepatitis and AIDS.

Those diseases are highly contagious blood diseases which offer the most serious risk of contamination during manual transfer of the contaminated blood. During that transfer, a clinician must hold a blood collection tube in his hand and force a contaminated needle through its top, thus increasing the risk for an accidental needle stick.

A need exists for a syringe-related device which may be used to collect blood samples in vacuum-type blood sample collecting tubes.

SUMMARY OF THE INVENTION

The present invention resides in a syringe-based blood collection system which has a plunger that provides an easy direct means of blood collection and blood transfer.

The principal object of the present invention is to allow manual aspiration of blood into a syringe and simultaneous transfer of blood to a vacuum-type blood collection tube from a central venous access such as Hickman external lumen or subcutaneous port.

A plunger body has a rubberized end on its lower extremity and a flange on its upper extremity. Screw threads and a rubber sleeve covered needle are connected to the upper extremity for use in connection with a blood tube holder and a vacuum-type blood collection tube.

The principal advantages of the present invention are found in its use, which eliminates the need to manually transfer blood from syringe to blood collections tubes, reducing the exposure to blood-contaminated needles, and therefore decreasing risk of needle sticks and diseases. The invention reduces hemolysis that occurs during transfer of blood; reduces the time for blood collection procedures and improves accuracy of blood test results.

The present invention eliminates the need to manually transfer blood from syringes and, consequently, reduces exposure to blood-contaminated needles.

An object of the invention is to decrease risk of needle sticks and disease, to improve quality of blood samples by reducing hemolysis which occurs during transfer of blood, to improve accuracy of blood tests results and to decrease time required for blood collection procedure.

Yet another object of the invention is to provide a vacuum plunger of the above nature which can easily be inserted into a syringe and connected with a blood tube holder and a vacuum-type blood collection tube, which is of such simple and inexpensive construction as to be readily disposable and expendable after use.

The present invention is created for use with currently manufactured syringes to provide improvements from previous methods of blood collection. The invention eliminates the need to manually transfer blood from syringes to blood collection tubes. Risk of needle sticks and disease is reduced by reducing exposure to blood-contaminated needles.

The invention improves the quality of blood samples by decreasing hemolysis due to manual transfer of blood and improves accuracy of blood tests results.

The invention provides a plunger body for replacing a plunger of a common syringe. The new plunger body is made of the same clear plastic material as is used to make conventional syringes and plungers. Dimensions are approximately the same as conventional syringe plungers. Exact outer dimensions are the same as in conventional plungers. An example of a plunger will work with a 10 cc (ml) syringe, but the plunger may be manufactured to fit into any size syringe.

In a preferred embodiment, a round plunger has a tubular opening which can match at least the diameter of a 21 gauge needle. The rubberized end enhances smoothness of movement and seals the plunger inside the syringe. On the opposite end, a flange provides a finger grip to hold for movement of the plunger manually. Screw threads next to the flange allow connection to a blood tube holder and are sized to fit that already manufactured device. The rubber covered needle operates well at a 21G size. The rubber covering retracts as a vacuum-type collection tube is pushed onto the needle.

In clinical use, the invention is used to access a central line, a subcutaneous port such as a Porta-Catheter, a Medi-Port, a Hickman catheter, or other catheter, or to perform venipuncture.

First, one connects the syringe with the fully-inserted new plunger to a proper gauge needle or a non-coring needle. Then a blood tube holder is attached, if desired. Then blood is aspirated into a syringe by sliding the plunger outward. Then a vacuum-type blood collection tube is pushed onto a rubber covered needle of the plunger to fill the tube. The blood collection tube is removed. The blood tube holder is removed, if used and if desired. The syringe, needle and plunger are removed from the central line, port or vein and are discarded in a sharps container.

The present invention replaces manual aspiration of blood from a central line, subcutaneous port or vein into a syringe with a conventional plunger, followed by manual transfer of blood into vacuum-type blood collection tubes.

This invention eliminates the need to manually transfer blood from syringes to blood collection tubes, reduces exposure to blood-contaminated needles, decreases risk of needle stick and disease, improves quality of blood samples due to reduced hemolysis which occurs during transfer of blood, improves accuracy of blood test results, and requires less time for blood collection procedures.

In a preferred embodiment of the invention the device is constructed to be used with currently manufactured syringes, blood tube holders and vacuum-type blood collection tubes.

In a preferred embodiment of the invention the device is made of the same clear plastic material used to make conventional plungers and its dimensions are the same as the dimensions of a conventional plunger.

These and further and other objects and features of the invention are apparent in the disclosure, which includes the above and ongoing written specification, with the claims and the drawings.

DETAILED DESCRIPTION OF THE DRAWINGS

Figure 1:
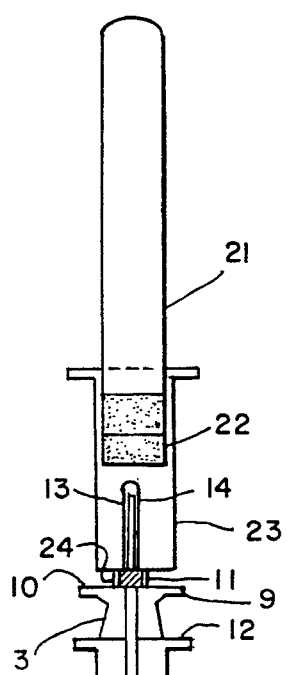
FIG. 1 is an assembled side elevational schematic view of the blood collecting syringe and plunger of the present invention, shown with a connected holder and vacuum-type collection tube.

Referring to the drawings, the blood collection system of the invention is referred to by the numeral 1. More particularly in FIGS. 1, 2, 3 and 4, it is shown that the plunger 3 is constructed of a body 4 with cruciform flanges 6. The body has a circular rubberized end 5 on its lower extremity and a flange 9 on its upper extremity. The flange 9 allows easy handling of the plunger when the plunger is pulled upwardly inside a syringe 15 through its open upper end 12, as shown in FIG. 1. The rubberized end 5 enhances smoothness of manual movement of the plunger, seals the plunger inside the syringe 15 and creates a reduced pressure as the plunger 3 is withdrawn outwardly or upwardly, as shown in the drawings.

A end-to-end tubular opening 7 extends through the plunger from its lower extremity 8 to its upper extremity 10 for allowing blood to flow from a syringe to a vacuum-type blood collection tube 21 by means of vacuum suction when the stopper 22 of tube 21 is pushed onto the needle 13, as shown in FIG. 1.

As shown in FIG. 1, screw threads 11 on the upper extremity 10 of the plunger 3 immediately after the flange 9 connect the boss 24 of a blood tube holder 23 screwed thereon, tightly securing the blood tube holder 23 around the transfer needle 13. A rubber covering 14 surrounds the needle 13, which extends upward from the boss 24 and the screw threads 11. The rubber covering 14 protects the needle, preventing its contamination and contamination of the plunger lumen and syringe and access needle while the latter is disposed. Cover 14 prevents accidental dropping of blood while it is being transferred through the plunger to the vacuum-type blood collection tube 21. Cover 14 recovers itself after tube is removed, then reducing the risk of accidental needle stick and consequent disease transfer.

Figure 2:
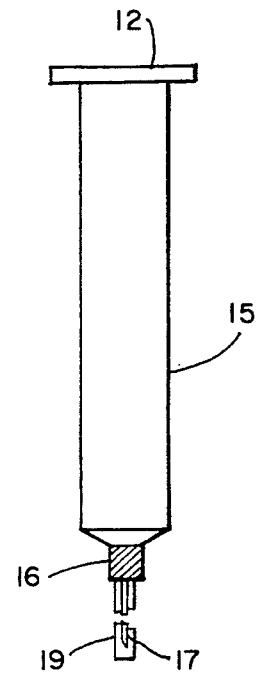
FIG. 2 is a schematic side elevational view of a syringe.

FIGS. 1 and 2 show a 10 cc syringe 15 to be used in connection with the vacuum plunger 3. The syringe 15 has an open upper end 12 and an internally threaded lower end 16 which is connected to an access needle 17 inside a protective plastic cap 19.

Figure 3:
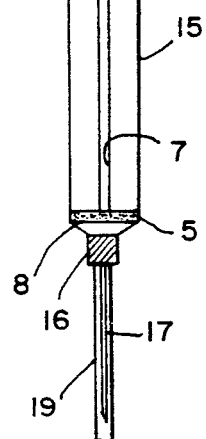
FIG. 3 is a schematic side elevational view of the plunger.

As shown in FIGS. 1 and 3, the rubber covered needle 13 is mounted in the blood tube holder 23. The blood tube holder 23 receives the vacuum-type blood collection tube 21. Its stoppered end is positioned over the rubber covered needle 13. Pressing tube 21 downward causes the needle to pierce the rubber covering 14, retracting it by means of friction of the stopper 22 along the needle 13. Blood freely flows from the syringe 15 through the end-to-end tubular channel 7 in plunger 3 and through needle 13 to the vacuum-type blood collection tube 21. Once observed, blood may be collected through the channel in the plunger without moving the plunger, simply by sliding the vacuum collection tube on the transfer needle.

In using the device of the present invention to collect blood from venipuncture, blood flowing into the syringe and plunger channel may be readily observed indicating a correct venipuncture. The plunger may be moved in the syringe to start or test blood flow without applying full vacuum. Full vacuum, such as from a collection tube, might be injurious or counterproductive in the case of a missed vein, which sometimes occurs. In the prior art device, blood flow cannot be observed until the puncturing of the vacuum-type collection tube stopper. Then, the full reduced pressure is applied to the access needle, even when a vein has not been entered. This is also costly since the blood tube vacuum is destroyed once its top is punctured to "test" for correct venipuncture and the needle is not inside a vein.

Figure 4:
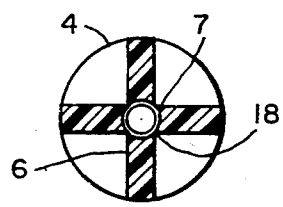
FIG. 4 is a cross-sectional view of the body of the plunger taken along lines IV—IV of FIG. 3.

In FIG. 4, a cross-sectional view of the body 4 of the vacuum plunger 3 is shown. The body of the device as shown has a round shape with cruciform flanges 6 that enter the plunger in the syringe. A tubular channel 7 extends through its central part 8.

Figure 5:
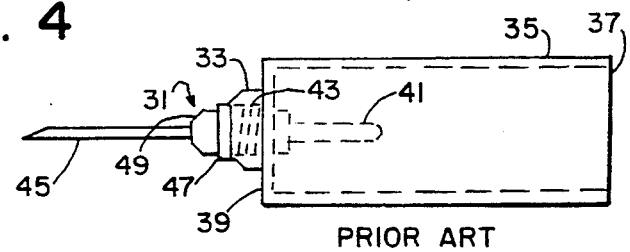
FIG. 5 is a side elevational view of a prior art vacuum tube holder with a double-ended needle.

FIG. 5 shows a double-ended needle 31 screwed into boss 33 of prior art vacuum-type blood sample collection tube holder 35. End 37 of the holder 35 is open. End 39 is closed around a central opening, which is surrounded by the internally threaded boss 33.

The double-ended needle 31 has an upper needle that is covered by a soft flexible rubber cover 41. A central portion 43 is threaded, and lower access needle 45 extends from a base 47 which has cruciform projections 49 for functionally engaging a rigid protective cap. A similar cap extends over the cover 41 before the second cap is removed to expose the cover 41 and central portion 43, which is screwed into the threaded boss 33.

While the invention has been described with reference to specific embodiments, modifications and variations of the invention may be constructed without departing from the scope of the invention, which is defined in the following claims.

I claim:

1. Blood sample collection and transfer apparatus, comprising a syringe with upper and lower needles, and a plunger for inserting in the syringe, the plunger having a plunger body with upper and lower extremities, having an end-to-end cylindrical opening, a rubberized end on the lower extremity, a flange on the upper extremity, the lower needle being connected to a lower end of the syringe, a rubber sleeve covering the upper needle on the upper extremity for using in connection with the syringe and the plunger, and a blood tube holder and a vacuum-type blood connection tube attached on the upper extremity surrounding the upper needle.

2. The apparatus of claim 1, wherein the plunger body end-to-end cylindrical opening has a size of at least 21 gauge for accommodating blood flow without destruction of blood cells and for carrying blood from the syringe to a vacuum-type blood collection tube.

3. The apparatus of claim 1, wherein the plunger body rubberized end on its lower extremity is for enhancing smoothness of movement of the plunger inside the syringe.

4. The apparatus of claim 1, wherein the plunger body further comprises screw threads located immediately above the flange, for receiving a blood tube holder screwed thereon and for securing the blood tube holder to the plunger.

5. The apparatus of claim 1, wherein a rubber sleeve covered needle is integrally formed above the screw threads for receiving a stoppered end of the collection tube and for retracting the rubber sleeve by friction as the stoppered end of the vacuum-type collection tube is slid onto the rubber covered needle.

6. A blood sample collection apparatus, comprising a syringe with a beveled open lumen venipuncture, or non-coring type subcutaneous port access needle, or injection type needle attached thereto on a lower end of the syringe, a plunger positioned in the syringe for collecting and transferring blood to a vacuum-type blood collection tube attached to an upper end of the syringe, the plunger having a plunger body with an end-to-end tubular opening, a rubberized lower end, and screw threads on an upper end of the plunger and a rubber sleeve covered transfer needle attached on the upper end of the plunger body.

7. The apparatus of claim 6, wherein the plunger is slidable in the syringe, and further comprising a blood tube holder mounted on the screw threads and a vacuum-type blood collection tube connected to the tube holder.

8. The apparatus of claim 6, wherein the plunger end-to-end tubular opening has a size of at least 21 gauge for allowing easy transferring of blood from the syringe through the transfer needle to a vacuum-type blood collection tube engaged on the transfer needle.

9. The apparatus of claim 6, wherein the rubberized end on a lower extremity of the plunger body enhances smoothness of movement and seals the plunger inside the syringe.

10. The apparatus of claim 6, further comprising a flange on the upper end of the plunger body for being held during manual movement of the plunger with respect to the syringe.

11. The apparatus of claim 6, further comprising complementary screw threads at the base of the rubber sleeve covered transfer needle for connecting the plunger with the blood sample collection tube holder.

12. The apparatus of claim 6, wherein the rubber sleeve covered transfer needle is integrally formed on an upper end of the plunger body and wherein the rubber sleeve retracts as a stopper of a vacuum-type blood sample collection tube is pushed against the rubber sleeve covered transfer needle.

13. A blood sample collection and transfer apparatus, comprising a syringe with first and second ends, with first and second needles at the first and second ends respectively, a plunger comprising a plunger body with upper and lower extremities, the plunger having an end-to-end lumen, and the lower extremity of the plunger having a rubberized end, and having a flange on the upper extremity, a protective sleeve for covering the second needle, the second needle being usable in connection with the syringe and plunger, further comprising a vacuum-type blood collection tube attached to the upper extremity of the plunger.

14. The apparatus of claim 13, wherein the lumen has a size of at least 21 gauge for accommodating blood flow without destruction of blood cells and for simultaneously transferring blood from the syringe to the vacuum-type blood collection tube.

15. The apparatus of claim 13, wherein the rubberized end of the plunger ensures a smooth movement of the plunger inside the syringe and forms a seal with an inner wall of the syringe so that blood can flow only through the lumen in the plunger.

16. The apparatus of claim 13, wherein the protective sleeve is of rubber material.

17. The apparatus of claim 13, further comprising a blood tube holder for attaching to the upper extremity of the plunger.

18. The apparatus of claim 17, further comprising the plunger body having screw threads adjacent the flange, for threadably receiving the blood tube holder and for securing the blood tube holder on the plunger.

19. The apparatus of claim 13, further comprising the second needle being integrally formed on the plunger along with the protective sleeve, for receiving a stoppered end of the collection tube, the protective sleeve being retractable by friction as the stoppered end of the vacuum-type collection tube is slid onto the sleeve covered needle.

20. A blood sample collection apparatus, comprising a syringe with a beveled open lumen venipuncture for receiving a non-coring type subcutaneous port access needle or an injection type needle attached thereto, a plunger positioned in the syringe for collecting and simultaneously transferring blood to a vacuum-type blood collection tube attached to the plunger, the plunger having a plunger body with an end-to-end tubular opening, a rubberized lower end and a protective sleeve covered transfer needle on an upper end of the plunger body.

21. The apparatus of claim 20, wherein the plunger is slidable in the syringe.

22. The apparatus of claim 20, further comprising a blood tube holder threadably mountable on plural screw threads at the upper end of the plunger.

23. The apparatus of claim 22, further comprising a vacuum-type blood collection tube connected to the tube holder.

24. The apparatus of claim 20, wherein the tubular opening has a size of at least 21 gauge for allowing easy transfer of blood from the syringe through the transfer needle to a container engageable on the transfer needle.

25. The apparatus of claim 20, wherein the rubberized end on a lower extremity of the plunger body enhances smooth movement of the plunger in the syringe and forms a seal around an inner wall of the syringe so that blood can flow only through the tubular opening of the plunger.

26. The apparatus of claim 20, further comprising a flange on the upper end of the plunger body for holding the plunger during manual movement of the plunger with respect to the syringe.

27. The apparatus of claim 20, further comprising the upper end of the plunger having screw threads for receiving complementary screw threads on a base of the transfer needle for connecting the plunger with a collection apparatus.

28. The apparatus of claim 20, wherein the protective sleeve covered transfer needle is integrally formed on an upper end of the plunger body.

29. The apparatus of claim 20, further comprising the vacuum-type blood sample collection tube having a stopper at one end, and wherein the protective sleeve retracts as the stopper is pushed on the sleeve covered transfer needle.

30. A method of blood sample collection and transfer without contamination with a syringe having first and second ends, with first and second needles at the first and second ends respectively, a plunger comprising a plunger body with an end-to-end lumen, a protective sleeve for covering the second needle, the second needle being usable in connection with the syringe and plunger, and a collection apparatus attached to the plunger, comprising the steps of:
inserting the first needle in a source of blood;
withdrawing the blood from the source;
flowing the blood from the syringe through the lumen of the plunger to the second needle; and
collecting the blood from the second needle into the collection apparatus.

31. The method of claim 30, further wherein the flowing comprises flowing the blood through the lumen having a size of at least 21 gauge for accommodating blood flow without destruction of blood cells and for simultaneously transferring blood from the syringe to the collection apparatus.

32. The method of claim 30, wherein the withdrawing further comprises moving the plunger within the syringe and ensuring a smooth movement of the plunger inside the syringe by means of a rubberized end of the plunger, the rubberized end forming a seal with an inner wall of the syringe for flowing blood only through the lumen in the plunger.

33. The method of claim 30, wherein the collecting further comprises attaching a blood tube holder to an upper extremity of the plunger and collecting blood by means of the holder.

34. The method of claim 30, wherein the collecting further comprises threadably attaching the collection apparatus on plural screw threads on an end of the plunger body and securing the collection apparatus on the plunger for directly receiving the blood collected in the syringe.

35. The method of claim 30, further comprising forming the second needle integrally on the plunger along with the protective sleeve.

36. The method of claim 30, further comprising forming the collection apparatus with a stoppered end, for slidably inserting on the protective sleeve and retracting the sleeve by friction, thereby protecting the second needle from contamination.

37. A method of blood sample collection with a syringe having a beveled open lumen venipuncture for receiving a non-coring type subcutaneous port access needle or an injection type needle attached thereto, a plunger positioned in the syringe, the plunger having a plunger body with an end-to-end tubular opening, a rubberized lower end and a protective sleeve covered transfer needle on an upper end of the plunger body, comprising the steps of:
attaching a vacuum-type blood collection tube to the transfer needle;
inserting the port access or injection type needle in a source of blood;
collecting blood in the syringe;
flowing blood by means of the tubular opening in the plunger;
transferring the flowing blood to the vacuum-type blood collection tube by means of the transfer needle;
transporting the collected blood in the tube by detaching the blood collection tube from the transfer needle.

38. The method of claim 37, wherein the attaching comprises threadably mounting a blood tube holder on plural screw threads at the upper end of the plunger.

39. The method of claim 37, wherein the flowing further comprises forming the tubular opening with a size of at least 21 gauge for facilitating easy flowing of blood from the syringe through the tubular opening and the transfer needle to a container engageable on the transfer needle.

40. The method of claim 37, wherein the flowing further comprises forming a lower extremity of the plunger body with a rubberized end for enhancing smooth movement of the plunger in the syringe and for forming a seal around an inner wall of the syringe to ensure blood flow only through the tubular opening of the plunger.

41. The method of claim 37, wherein the collecting further comprises forming a flange on the upper end of the plunger body for holding the plunger during manual movement of the plunger with respect to the syringe.

42. The method of claim 37, wherein the attaching further comprises threadably attaching the upper end of the plunger with a base of the transfer needle for connecting and securing the plunger with a collection apparatus.

43. The method of claim 37, further comprising forming the protective sleeve covered transfer needle integrally on an upper end of the plunger body.

44. The method of claim 37, further comprising forming the vacuum-type blood sample collection tube with a stopper at one end for inserting on the transfer needle, wherein the protective sleeve retracts as the stopper is pushed on the sleeve covered transfer needle.

* * * * *